United States Patent
Algawi et al.

(10) Patent No.: US 12,427,239 B2
(45) Date of Patent: Sep. 30, 2025

(54) PULSE WIDTH MODULATION (PWM) OPERATED VACUUM RELIEF VALVE IN CONJUNCTION WITH AN ANTI-VACUUM SURGE (AVS) MODULE

(71) Applicant: JOHNSON & JOHNSON SURGICAL VISION, INC., Irvine, CA (US)

(72) Inventors: Yehuda Algawi, Binyamina (IL); Assaf Govari, Haifa (IL); Ilya Sitnitsky, Nahariya (IL); Eran Aharon, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 811 days.

(21) Appl. No.: 17/563,766

(22) Filed: Dec. 28, 2021

(65) Prior Publication Data
US 2023/0201443 A1    Jun. 29, 2023

(51) Int. Cl.
*A61M 1/00*      (2006.01)
*A61F 9/007*     (2006.01)
*A61B 17/32*     (2006.01)

(52) U.S. Cl.
CPC ......... *A61M 1/743* (2021.05); *A61F 9/00745* (2013.01); *A61M 1/73* (2021.05); *A61M 1/75* (2021.05); *A61B 2017/32007* (2017.08)

(58) Field of Classification Search
CPC .......... A61M 1/743; A61M 1/73; A61M 1/75; A61M 1/732; A61M 1/76; A61M 2210/0612; A61F 9/00745; A61B 2017/32007
See application file for complete search history.

(56) References Cited

U.S. PATENT DOCUMENTS

| | | | |
|---|---|---|---|
| 4,041,947 A | 8/1977 | Weiss et al. | |
| 5,094,260 A * | 3/1992 | Stuart | G05D 16/2053 137/596.17 |
| 5,725,495 A * | 3/1998 | Strukel | A61M 1/7413 604/35 |
| 6,425,883 B1 * | 7/2002 | Urich | A61M 1/74 604/35 |
| 9,549,850 B2 * | 1/2017 | Sorensen | A61F 9/00763 |
| 2008/0319374 A1 * | 12/2008 | Zacharias | A61M 1/743 604/22 |

(Continued)

FOREIGN PATENT DOCUMENTS

EP    2164435 B1    8/2012

*Primary Examiner* — Phillip A Gray

(57) ABSTRACT

A system for controlling aspiration of a phacoemulsification probe inserted into an eye includes an anti-vacuum surge (AVS) module, one or more sensors, a vacuum relief valve, and a processor. The AVS module is coupled with an aspiration channel of the probe and is configured to mitigate vacuum surges in the channel by regulating flow via the channel. The one or more sensors are configured to measure fluid parameters in the channel. The vacuum relief valve, which is fluidly coupled with the channel, is configured to controllably relieve vacuum in the channel. The processor is configured to identify a change in at least one of the fluid parameters by reading at least one of the one or more sensors, and, responsively to an identified change in fluid parameters, operate the vacuum relief valve using pulse width modulation (PWM) to maintain a pressure in the channel within a predefined range.

8 Claims, 3 Drawing Sheets

(56) References Cited

U.S. PATENT DOCUMENTS

| | | |
|---|---|---|
| 2009/0163853 A1 | 6/2009 | Cull et al. |
| 2010/0030134 A1* | 2/2010 | Fitzgerald ............... A61M 1/77 |
| | | 604/35 |
| 2011/0060300 A1* | 3/2011 | Weig ....................... A61F 5/451 |
| | | 604/319 |
| 2014/0323953 A1* | 10/2014 | Sorensen ............ A61F 9/00745 |
| | | 604/35 |
| 2017/0087283 A1* | 3/2017 | Ovchinnikov ...... A61F 9/00745 |
| 2018/0049921 A1 | 2/2018 | Sorensen et al. |
| 2019/0282401 A1* | 9/2019 | Sorensen ................ A61M 1/74 |
| 2020/0022841 A1 | 1/2020 | Chamness et al. |
| 2020/0337900 A1 | 10/2020 | Nazarifar et al. |
| 2022/0192876 A1* | 6/2022 | Algawi ............... A61F 9/00745 |

\* cited by examiner

PULSE WIDTH MODULATION (PWM) OPERATED VACUUM RELIEF VALVE IN CONJUNCTION WITH AN ANTI-VACUUM SURGE (AVS) MODULE

FIELD OF THE DISCLOSURE

The present disclosure relates generally to phacoemulsification systems and probes, and particularly to systems for aspiration and irrigation control.

BACKGROUND OF THE DISCLOSURE

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

Various techniques of irrigation and aspiration control with medical probes were proposed in the patent literature. For example, U.S. Patent Application Publication 2017/0087283 describes a surgical system comprising a hand piece, an irrigation conduit in fluid communication with the hand piece to carry fluid toward a surgical site, an aspiration conduit in fluid communication with the hand piece to carry fluid away from the surgical site, a pump interfacing with the aspiration conduit, the pump to create a vacuum pressure in the aspiration conduit to draw fluid through the aspiration conduit, a vacuum relief valve in fluid communication with the aspiration conduit to relieve the vacuum pressure in the aspiration conduit, a pressure sensor to detect a pressure associated with the surgical site, a controller in communication with the vacuum relief valve and the pressure sensor to control the vacuum relief valve to decrease the vacuum pressure in the aspiration conduit when the pressure detected by the pressure sensor is less than a first pressure threshold. In some exemplary examples, the vacuum relief valve is controlled to close without a measurement taken from an aspiration sensor. For example, in some exemplary examples, the vacuum relief valve reduces the vacuum pressure within the aspiration conduit by rapidly pulsing between an open position and a closed position for a predetermined period of time.

The present disclosure will be more fully understood from the following detailed description of the examples thereof, taken together with the drawings in which:

DETAILED DESCRIPTION OF EXAMPLES

Overview

Figure 1:
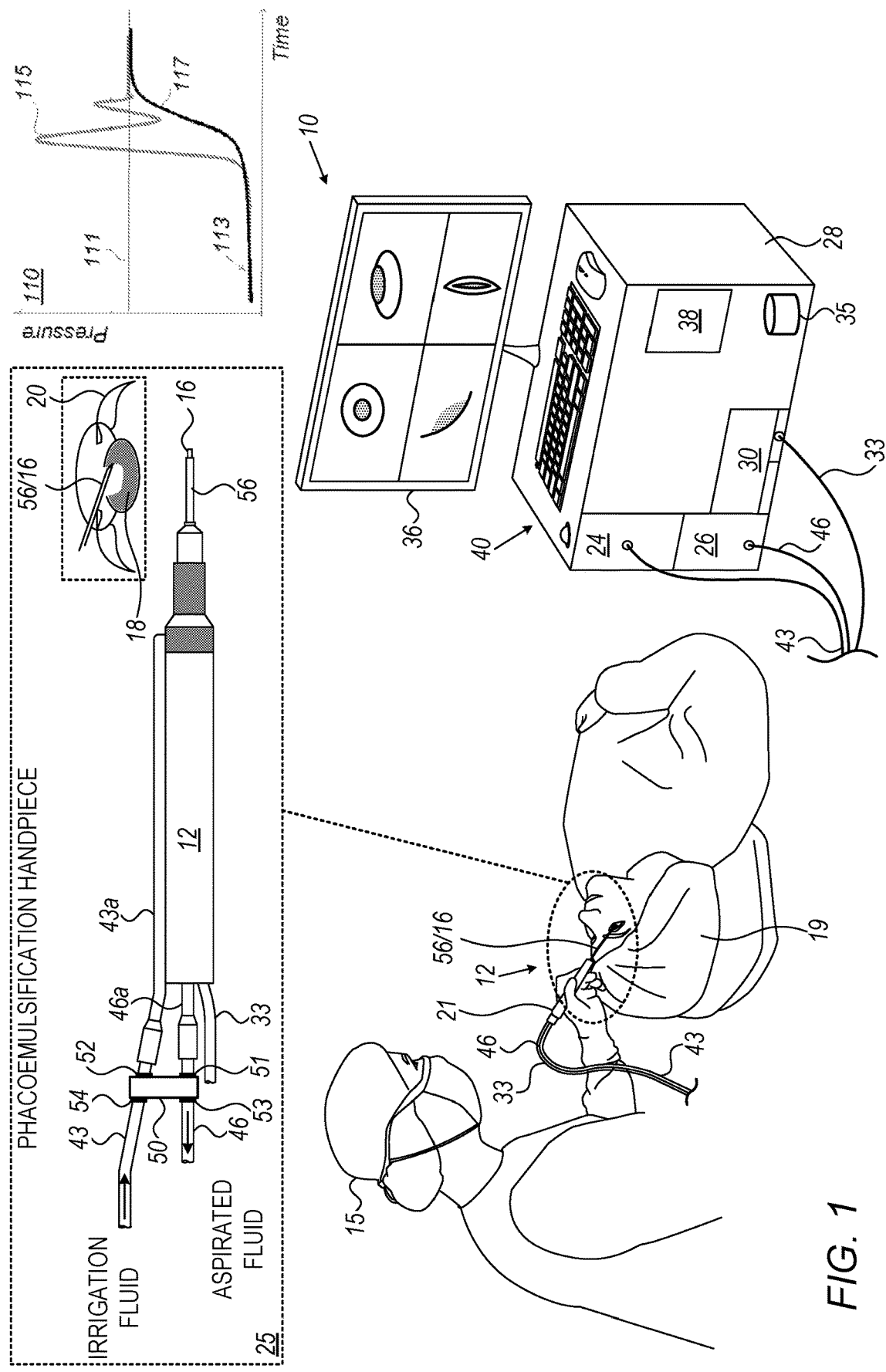
FIG. 1 is a schematic, pictorial view, along with an orthographic side view, of a phacoemulsification apparatus comprising an aspiration and irrigation control module, in accordance with an example of the present disclosure.

During phacoemulsification the emulsified lens particles are aspirated. When a particle blocks the inlet of the aspiration channel the vacuum in the line increases. When the line later becomes unblocked (e.g., when the particle is subsequently sucked into the line), the high vacuum in the line causes an aspiration surge with potentially traumatic consequences to the eye.

A recent solution to the problem of vacuum surge is described in U.S. patent application Ser. No. 17/130,409, filed on Dec. 22, 2020, and titled, "A module for Aspiration and Irrigation Control," whose disclosure is incorporated herein by reference. The application discloses an anti-vacuum surge (AVS) module coupled with a phacoemulsification probe, which prevents a sudden vacuum increase being transferred to the eye when an occlusion breaks. For example, the module can mitigate the vacuum surge by closing off a connection from the aspiration channel to the eye at the distal side of the module.

During the above-described mitigation, a vacuum pump in the phacoemulsification system's console may continue to operate, so that a relatively high vacuum is maintained in the proximal side of the AVS module. This high vacuum can transfer abruptly to the eye when the AVS module reverts to its "normal" ongoing operating format (where the irrigation and vacuum lines are directly connected to the eye), and the abrupt transfer may be traumatic. To avoid this scenario, a system may use a venting valve that lets ambient air to flow into the vacuum line. However, using a venting valve to dampen a vacuum surge may cause an opposite phenomenon of sudden air pressure rising in the line, which is now opened in the direction of the eye after the AVS module reverted to its "normal" ongoing operating format. This pressure pulse may cause emulsified material (particles) in the aspiration channel to fly back into the eye with harmful consequences.

Examples of the present disclosure that are described hereinafter incorporate a specially controlled vacuum relief valve (also referred to as a venting valve) into the vacuum line. Before the AVS module reverts to its normal operating format that may cause a sudden rise in air pressure, the valve is opened-and-closed intermittently with Pulse Width Modulation (PWM), allowing air to enter the vacuum line in a highly controlled manner, while the pump may continue to operate. Though a given amount of air still remains in the line, the AVS module can safely revert to its normal operating format, so that there is neither an abrupt high vacuum transfer to the eye nor a pressure wave. The vacuum relief valve is therefore carefully controlled for two purposes:

1. To activate (open) the vacuum relief valve only after the AVS is activated.

2. To regulate the pressure increase so that it does not surpass a defined threshold (e.g., 50 mmHg). The pressure is regulated based on PWM-activation of the vacuum relief valve in pulses while periodically sensing the pressure in the aspiration line (e.g., using a pressure sensor in the handpiece or in a disposable module attached to the handpiece, e.g., an AVS module). In this way, as noted above, any risk of a stray pressure wave traveling in the direction of the eye (after a vacuum surge has been suppressed) is prevented.

The disclosed PWM-operated valve can be located at the console of the phacoemulsification system, or at any suitable position along the aspiration line, and even incorporated into the AVS module itself. Accordingly, different processors of the system may PWM-control the valve, as described below.

System Description

FIG. 1 is a schematic, pictorial view, along with an orthographic side view, of a phacoemulsification apparatus 10 comprising an aspiration and irrigation control module 50, in accordance with an example of the present disclosure.

As seen in the pictorial view of phacoemulsification apparatus 10, and in inset 25, a phacoemulsification probe 12 (e.g., a handpiece) comprises a needle 16 and a coaxial irrigation sleeve 56 that at least partially surrounds needle 16 and creates a fluid pathway between the external wall of the needle and the internal wall of the irrigation sleeve, where needle 16 is hollow to provide an aspiration channel. Moreover, the irrigation sleeve may have one or more side ports at or near the distal end to allow irrigation fluid to flow toward the distal end of the handpiece through the fluid pathway and out of the port(s).

Needle 16 is configured for insertion into a lens capsule 18 of an eye 20 of a patient 19 by a physician 15 to remove a cataract. While the needle 16 (and irrigation sleeve 56) are shown in inset 25 as a straight object, any suitable needle may be used with phacoemulsification probe 12, for example, a curved or bent tip needle commercially available from Johnson & Johnson Surgical Vision, Inc., Santa Ana, CA, USA.

In the shown example, during the phacoemulsification procedure a pumping subsystem 24 comprised in a console 28 pumps irrigation fluid from an irrigation reservoir (not shown) to the irrigation sleeve 56 to irrigate the eye. The fluid is pumped via an irrigation tubing line 43 running from the console 28 to an irrigation channel 43a of probe 12. Eye fluid and waste matter (e.g., emulsified parts of the cataract) are aspirated via hollow needle 16 to a collection receptacle (not shown) by a pumping subsystem 26, also comprised in console 28, using an aspiration tubing line 46 running from aspiration channel 46a of probe 12 to console 28. In another example, the pumping subsystem 24 may be coupled or replaced with a gravity-fed irrigation source such as a balanced salt solution bottle/bag.

Apparatus 10 includes standalone disposable detachable add-on module 50, coupled via fluid connectors 51-54, to control aspiration and irrigation flow rates to reduce risks to eye 20 from irregular performance of aspiration and/or irrigation in probe 12, such as from a vacuum surge. To this end, the disclosed module 50 establishes variable fluid communication between aspiration channel 46a and irrigation channel 43a to control the flow of fluid between the two channels/tubing lines, so as to maintain pressures in the two channels/tubing lines within predefined limits. Moreover, module 50 can discontinue aspiration in parallel in order to provide a fast response (e.g., within several milliseconds) to a detected vacuum surge. Module 50 has its own processor and can be used with existing phacoemulsification systems as a disposable element that improves control over intraocular pressure (IOP) during the surgical cataract removal procedure.

A graph 110 at the top-right of FIG. 1 shows that, during restoration of vacuum level from a vacuum surge level 113 to a nominal vacuum level 111, a potentially eye-harmful pressure pulse 115 may occur. The disclosed PWM-operated valve described in FIG. 2 eliminates the pulse and provide moderated increase of pressure in the general form of pressure curve 117.

Phacoemulsification probe 12 includes other elements (not shown), such as one or more piezoelectric crystals coupled with a horn to drive vibration of needle 16. The piezoelectric crystal is configured to vibrate needle 16 in a resonant vibration mode. The vibration of needle 16 is used to break a cataract into small pieces during a phacoemulsification procedure. Console 28 comprises a piezoelectric drive module 30, coupled with the piezoelectric crystal, using electrical wiring running in a cable 33. Drive module 30 is controlled by a processor 38 and conveys processor-controlled driving signals via cable 33 to, for example, maintain needle 16 at maximal vibration amplitude. The drive module may be realized in hardware or software, for example, in a proportional-integral-derivative (PID) control architecture.

Processor 38 may receive user-based commands via a user interface 40, which may include setting a vibration mode, duty cycle, and/or frequency of the piezoelectric crystal, and setting or adjusting an irrigation and/or aspiration rate of the pumping subsystems 24/26. In an example, user interface 40 and display 36 may be combined as a single touch screen graphical user interface. In an example, the physician uses a foot pedal (not shown) as a means of control. Additionally or alternatively, processor 38 may receive the user-based commands from controls located in a handle 21 of probe 12.

Some or all of the functions of processor 38 may be combined in a single physical component or, alternatively, implemented using multiple physical components. These physical components may comprise hard-wired or programmable devices, or a combination of the two. In some examples, at least some of the functions of processor 38 may be carried out by suitable software stored in a memory 35 (as shown in FIG. 1). This software may be downloaded to a device in electronic form, over a network, for example. Alternatively or additionally, the software may be stored in tangible, non-transitory computer-readable storage media, such as optical, magnetic, or electronic memory.

The apparatus shown in FIG. 1 may include further elements which are omitted for clarity of presentation. For example, physician 15 typically performs the procedure using a stereomicroscope or magnifying glasses, neither of which are shown. Physician 15 may use other surgical tools in addition to probe 12, which are also not shown in order to maintain clarity and simplicity of presentation.

In some examples, a different type of AVS module can be used that is coupled only with the aspiration part of the system (i.e., without involving irrigation).

PWM-Operated Vacuum Relief Valve in Conjunction with an AVS Module

Figure 2:
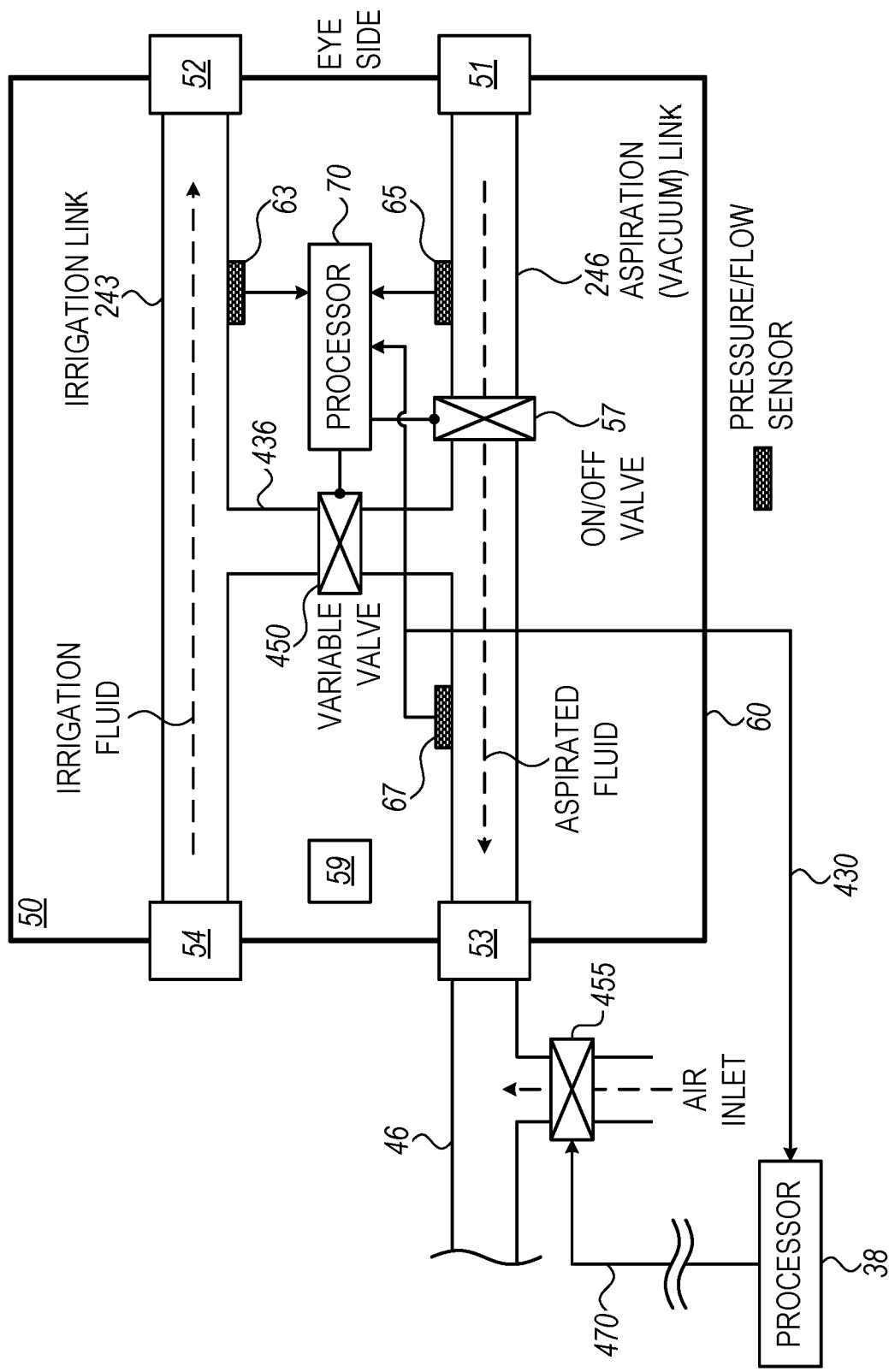
FIG. 2 is a schematic block diagram of a pulse width modulation (PWM) operated vacuum relief valve externally coupled with the aspiration and irrigation control module of FIG. 1, in accordance with an example of the present disclosure.

FIG. 2 is a schematic block diagram of a pulse width modulation (PWM) operated vacuum relief valve 455 externally coupled with module 50 of FIG. 1, in accordance with an example of the present disclosure.

In the shown example, module 50 includes a battery 59 inside a package 60 of the module to power a processor, sensors, and electromechanical valves. In general, package 60 includes either an internal power source (e.g., battery 59) or power transfer element (e.g., a power socket or a wireless power transfer circuit).

As seen, package 60 includes connectors 51-54 fitted on the package that are configured to couple the aspiration and irrigation channels of a probe (46a and 43a via connectors 51 and 52, respectively), and to couple the respective aspiration and irrigation lines of the phacoemulsification system (46 and 43 via connectors 53 and 54, respectively) to the module. In other examples, the power source does not come from a battery, but rather from an external source using, for example, a socket incorporated in package 60.

Inside package 60 there is an irrigation link 243 to flow irrigation fluid from line 43 into irrigation channel 43a, and an aspiration link 246 to remove material from aspiration channel 46a into aspiration line 46. Furthermore, irrigation link 243 is fluidly coupled with aspiration link 246 via a bypass channel 436. As seen, a diversion (processor-controlled) variable valve 450 on bypass channel 436 is configured to control a level of fluid communication between irrigation link 243 and aspiration link 246. In other examples, an AVS module is provided which does not include the bypass channel 436.

An aspiration (processor-controlled) valve 57 is configured to open or close aspiration link 246 at a distal portion of thereof, to, for example, immediately suppress a vacuum surge until regulated flows are restored, for example, by the action of valve 450, and/or by using the disclosed PWM-controlled venting valve 455, whose operation is described below.

To provide feedback, a sensor 63, such as a pressure sensor or a flow sensor, is coupled with irrigation link 243 to measure the actual irrigation fluid parameters that affect the eye (e.g., pressure or flow rate) in irrigation link 243 distally to bypass channel 436. A sensor 65 (such as a pressure sensor or a vacuum sensor) similarly measures the aspiration pressure in aspiration link 246 distally to bypass channel 436. An additional sensor 67 similarly measures the flow/pressure in aspiration link 246 proximally to bypass channel 436. The pressure/flow and pressure/vacuum measurements are performed close to aspiration inlet connector 51 and irrigation outlet connector 52, respectively, by respective sensors 65 and 63, so as to provide an accurate indication of the actual pressures experienced by an eye and provide quick response time to a control loop of module 50.

Based on the fluid pressure/flow measured by sensors 63-67, a processor 70 included in module 50 adaptively adjusts an opening of bypass channel 436 by adjusting valve 450, and, in coordination, closes or opens aspiration valve 57. This coordinated operation of the valves maintains pressure/flow readings within predefined limits throughout the surgical procedure, without any dependency on external controls (e.g., of a legacy system to which module 50 is added). Additionally or alternatively, pressure/flow readings are maintained using the below-described PWM-operated vacuum relief valve, in particular for preventing an occurrence of a stray pressure wave that can harm the eye during restoration of nominal aspiration performance.

In particular, in some examples, a different type of AVS module can be used that is coupled only with the aspiration part of the system (i.e., without involving irrigation). In such an AVS module there is no diversion of irrigation via a bypass channel, and aspiration flow is solely determined by elements on the aspiration line/channel, such as the aspiration pump and valves 455 and 57.

As seen, vacuum relief valve 455 can couple aspiration line 46 to ambient air to allow air flow into aspiration line 46 in a controlled manner. The vacuum relief valve 455 is applied after the AVS module is activated, and this reoperation of the AVS module includes aspiration pump valve 57 being opened, in order to regulate the increased rate of pressure so that it does not surpass a defined threshold (e.g., 50 mmHg). For this purpose, processor 38 periodically (e.g., every few milliseconds) receives pressure-indicative readings from sensor 67 via a data line 430. Based on sensor 67 readings, processor 38 PWM activates, via command line 470, vacuum relief valve 455. This minimizes the venting of a stray air pressure wave traveling in aspiration line 46 in the direction of the eye (after a vacuum surge is suppressed).

The example shown in FIG. 2 is chosen purely for the sake of conceptual clarity. For example, other examples are possible, such as those that use different external control hardware than processor 38. Furthermore, sensor readings may be provided from other sensors, either inside module 50, such as sensor 65, or outside of the module, e.g., from a sensor located in handpiece 12. In other examples, the processor is located outside the module, such as in the console, and is electrically connected to the module with a cable or wirelessly.

Figure 3:
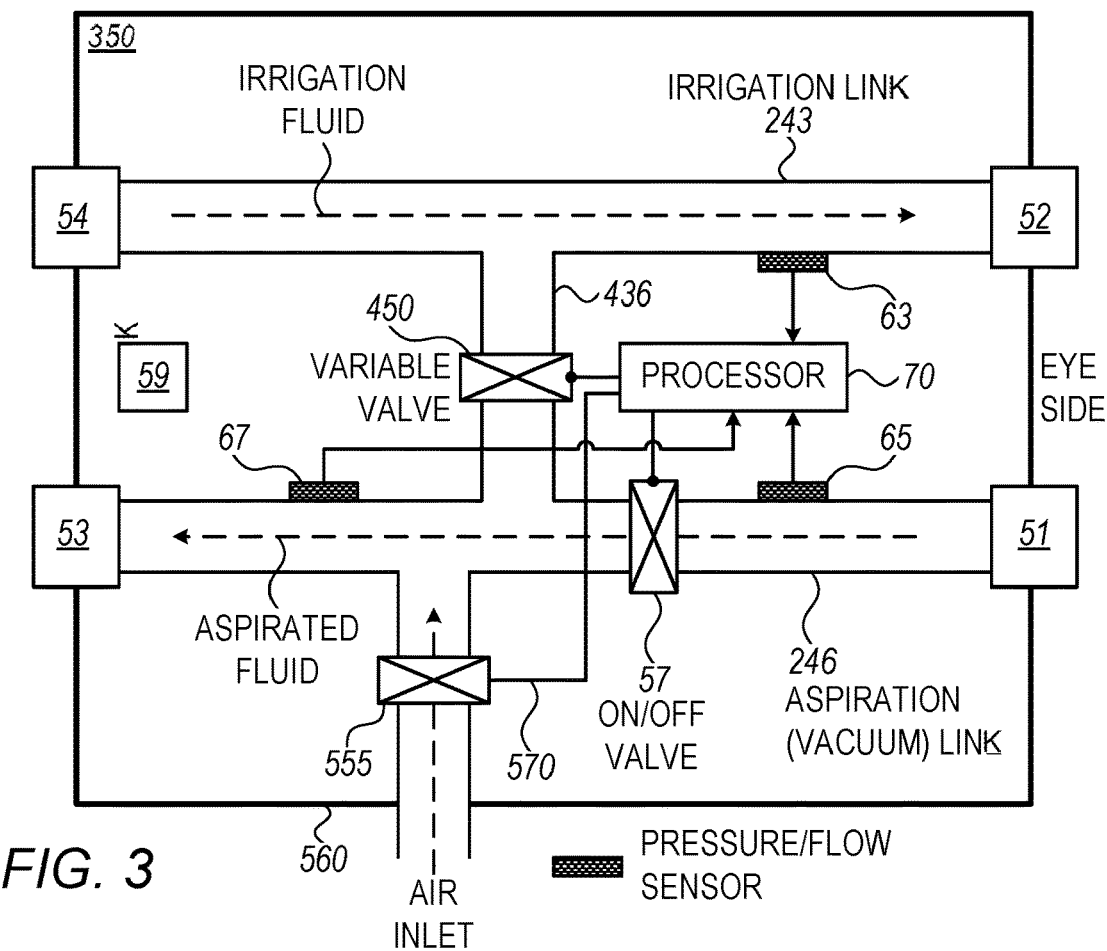
FIG. 3 is a schematic block diagram of a PWM-operated vacuum relief valve incorporated into the aspiration and irrigation control module of FIG. 1, in accordance with an example of the present disclosure.

FIG. 3 is a schematic block diagram of a PWM-operated vacuum relief valve 555 incorporated into module 50 of FIG. 1, in accordance with an example of the present disclosure. This provides a relief-valve incorporated AVS module 350. A package 560 is adapted with an opening in the package to allow ambient air access to the air inlet of valve 555.

As seen, vacuum relief valve 555 can couple aspiration link 246 with ambient air to allow air flow into aspiration link 246 in a controlled manner. The vacuum relief valve 555 is applied after the AVS module 350 is activated, and this reoperation of the AVS module 350 includes valve 57 being opened.

As further seen, processor 70 inside package 560 controls valve 555 via a command line 570. Other elements of module 50 are described in FIG. 2. In other examples, the processor is located outside the module, such as in the console, and is electrically connected to the module with a cable or wirelessly.

In the shown example, processor 70 periodically receives (e.g., every few milliseconds) pressure-indicative readings from sensor 67 and/or sensor 65. Based on readings of sensors 67 and/or 65, processor 70 activates, via command line 570, vacuum relief valve 555 in PWM mode. This minimizes a stray air venting pressure wave traveling in aspiration link 246 in the direction of the eye (after a vacuum surge is suppressed).

As already noted with the example of FIG. 2, in some examples a different type of AVS module can be used in FIG. 3, that is coupled only with the aspiration part of the system (i.e., without involving irrigation). In such an AVS module there is no diversion of irrigation via a bypass channel, and aspiration flow is determined solely by elements on the aspiration line/channel, such as the aspiration pump and valves 555 and 57.

Method of PWM-Operating Vacuum Relief Valve with an AVS Module

Figure 4:
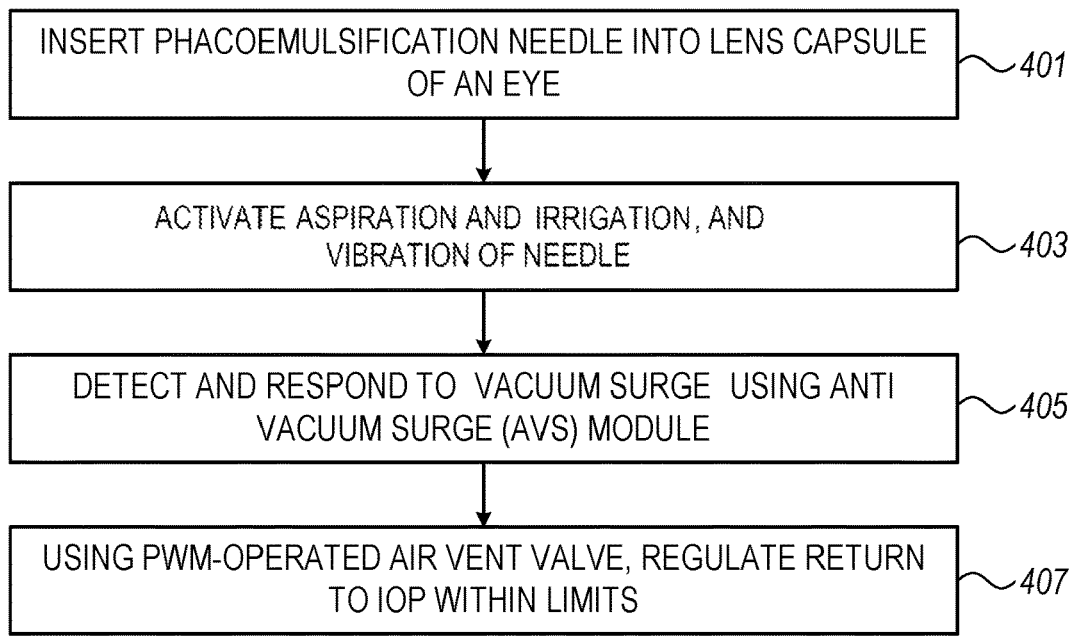
FIG. 4 is a flow chart schematically illustrating a method for overcoming a vacuum surge using the PWM-operated vacuum relief valve of either FIG. 2 or 3, in accordance with some examples of the present disclosure.

FIG. 4 is a flow chart schematically illustrating a method for overcoming a vacuum surge using the PWM-operated vacuum relief valve of either FIG. 2 or 3 (e.g., valve 455 or valve 555), in accordance with some examples of the present disclosure. The process begins with physician 15 inserting phacoemulsification needle 16 of probe 12 into a lens capsule 18 of an eye 20, at a phacoemulsification needle insertion step 401.

At a phacoemulsification step 403, physician 15 presses a foot pedal to a first position to activate aspiration and subsequently to a second position to activate irrigation, and finally, when the foot pedal is pressed and placed in a third position, the needle 16 is vibrated to perform the phacoemulsification.

Beforehand, processor 70 verifies (e.g., based on null readings from the sensor upon powering up module 50) that valves 450 and 57 are at default positions (in which valve 57 is open, and valve 450 is closed).

During this process, processor 70 receives pressure readings from sensors 63, 65, and/or 67. However, the process works also using only one sensor on the aspiration link, such as sensor 67, which, when valve 57 is closed, reads pressure (or vacuum level) in the aspiration link and/or aspiration channel of probe 12. If an aspiration blockage occurs, as determined by processor 70 that is based on, for example, readings from sensor 65 being below predefined values (or from sensor 67 alone, if sensor 65 is not included), processor 70 operates module 50 to overcome vacuum surge (e.g., by closing valve 57) in a vacuum surge response step 405.

After the AVS module is operated in step 405, and this reoperation of the AVS includes valve 57 being opened, either processor 38 or 70 (depending on the example used, e.g., FIG. 2 or FIG. 3) PWM-operates the respective vacuum relief valve 455 or 555, at a pressure regulation step 407, to maintain a pressure in the aspiration channel within a predefined range (i.e., to avoid a subsequent pressure wave to the eye from the venting process). In other examples, the processor can operate respective vacuum relief valve 455 or 555 without using PWM, for example by using readings from sensor 67 to close vacuum relief valve 455 or 555 if the rate of pressure increase is too fast.

Example 1

A system for controlling aspiration of a phacoemulsification probe (12) inserted into an eye, the system including an anti-vacuum surge (AVS) module (50), one or more sensors (63, 65, 67), a vacuum relief valve (455), and a processor (70). The AVS module is coupled with an aspiration channel of the phacoemulsification probe and is configured to mitigate vacuum surges in the aspiration channel (46a) by regulating flow via the aspiration channel. The one or more sensors are configured to measure fluid parameters in the aspiration channel. The vacuum relief valve, which is fluidly coupled with the aspiration channel, is configured to controllably relieve vacuum in the aspiration channel. The processor is in communication with the one or more sensors, and configured to identify a change in at least one of the fluid parameters by reading at least one of the one or more sensors, and, in response to the identified change in the at least one of the fluid parameters, operate the vacuum relief valve using pulse width modulation (PWM) to maintain a pressure in the aspiration channel within a predefined range.

Example 2

The system according to example 1, wherein the at least one of the fluid parameters are selected from the group consisting of vacuum, pressure, and flow, and wherein the identified change of the at least one of the fluid parameters is indicative of a release of a blockage in the aspiration channel.

Example 3

The system according to example 1 or example 2, wherein the processor is configured to identify the change in the at least one of the fluid parameters by detecting an increase in vacuum or pressure in the aspiration channel or in an aspiration line coupled with the aspiration channel.

Example 4

The system according to any examples 1 through 3, wherein the processor is configured to begin operating the vacuum relief valve only after the AVS module was reoperated.

Example 5

The system according to any examples 1 through 4, wherein the vacuum relief valve is located externally to the AVS module.

Example 6

The system according to any examples 1 through 4, wherein the vacuum relief valve is incorporated in the AVS module.

Example 7

The system according to any examples 1 through 6, wherein the processor is external to the AVS module.

Example 8

The system according to any examples 1 through 6, wherein the processor is incorporated in the AVS module.

Example 9

A method for controlling aspiration of a phacoemulsification probe inserted into an eye, the method including coupling an anti-vacuum surge (AVS) module with an aspiration channel of the phacoemulsification probe, the AVS module configured to mitigate vacuum surges in the aspiration channel by regulating flow via the aspiration channel. Using one or more sensors, fluid parameters are measured in the aspiration channel. A vacuum relief valve is fluidly coupled with the aspiration channel, the vacuum relief valve configured to controllably relieve vacuum in the aspiration channel. Using a processor in communication with the one or more sensors, a change is identified in at least one of the fluid parameters by reading at least one of the one or more sensors, and, in response to the identified change in the at least one of the fluid parameters, the vacuum relief valve is operated using pulse width modulation (PWM) to maintain a pressure in the aspiration channel within a predefined range.

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for controlling aspiration of a phacoemulsification probe inserted into an eye, the system comprising:
   a vacuum relief valve coupled to ambient air, which is fluidly coupled with an aspiration channel of the phacoemulsification probe and is configured to mitigate vacuum surges in the aspiration channel by regulating flow via the aspiration channel;
   an aspiration valve coupled with an aspiration line, wherein the aspiration line is located between the phacoemulsification probe and a console and is fluidly coupled with the aspiration channel;
   one or more sensors configured to measure fluid parameters in the aspiration channel;
   and
   a processor in communication with the one or more sensors and the vacuum relief valve, the processor configured to identify a change in at least one of the fluid parameters by reading at least one of the one or more sensors, and, in response to the identified change in the at least one of the fluid parameters, operate the vacuum relief valve using pulse width modulation (PWM) to maintain a pressure in the aspiration channel within a predefined range;
   wherein the aspiration valve is located between the vacuum relief valve and the phacoemulsification probe.

2. The system according to claim 1, wherein the at least one of the fluid parameters are selected from the group consisting of vacuum, pressure, and flow, and wherein the identified change of the at least one of the fluid parameters is indicative of a release of a blockage in the aspiration channel.

3. The system according to claim 1, wherein the processor is configured to identify the change in the at least one of the fluid parameters by detecting an increase in vacuum or pressure in the aspiration channel or in the aspiration line.

4. The system according to claim 1, wherein the processor is configured to begin operating the vacuum relief valve only after the aspiration valve is opened.

5. A method for controlling aspiration of a phacoemulsification probe inserted into an eye, the method comprising:
   fluidly coupling a vacuum relief valve with an aspiration channel of the phacoemulsification probe, the vacuum relief valve coupled to ambient air and configured to mitigate vacuum surges in the aspiration channel by regulating flow via the aspiration channel;
   fluidly coupling an aspiration valve with an aspiration line, wherein the aspiration line is located between the phacoemulsification probe and a console, and is fluidly coupled with the aspiration channel;
   using one or more sensors, to measure fluid parameters in the aspiration channel;
   and
   using a processor in communication with the one or more sensors and the vacuum relief valve to identify a change in at least one of the fluid parameters by reading at least one of the one or more sensors; and
   in response to the identified change in the at least one of the fluid parameters, operating the vacuum relief valve using pulse width modulation (PWM) to maintain a pressure in the aspiration channel within a predefined range; wherein
   the aspiration valve is located between the vacuum relief valve and the phacoemulsification probe.

6. The method according to claim 5, wherein the at least one of the fluid parameters are selected from the group consisting of vacuum, pressure, and flow, and wherein the identified change of the at least one of the fluid parameters is indicative of a release of a blockage in the aspiration channel.

7. The method according to claim 5, wherein identifying the change in the at least one of the fluid parameters comprises detecting an increase in vacuum or pressure in the aspiration channel or in the aspiration line.

8. The method according to claim 5, wherein the vacuum relief valve is operated only after the aspiration valve is opened.

* * * * *